US00PP08198P

United States Patent [19]

Gorvel

[11] Patent Number: Plant 8,198

[45] Date of Patent: Apr. 6, 1993

[54] DWARF, VARIEGATED SCHEFFLERA NAMED COVEEN

[75] Inventor: Ernest A. Gorvel, Stuart, Fla.

[73] Assignee: Florida Cuttings, Inc., Stuart, Fla.

[21] Appl. No.: 611,402

[22] Filed: Nov. 9, 1990

[51] Int. Cl.[5] ..... A01H 5/00

[52] U.S. Cl. ..... Plt./88.1

[58] Field of Search ..... Plt./88, 88.1

[56] References Cited

U.S. PATENT DOCUMENTS

P.P. 5,541 8/1985 Resch ..... Plt. 88

P.P. 6,134 3/1988 Gorvel ..... Plt. 88

*Primary Examiner*—James R. Feyrer

*Attorney, Agent, or Firm*—Foley & Lardner

[57] ABSTRACT

The new variety of Schefflera, named Coveen, is characterized by a mixed foliage of dark green leaves, bright yellow leaves and variegated, green/yellow leaves.

5 Drawing Sheets

BACKGROUND OF THE INVENTION

The present invention relates to a new and distinctive cultivar of Schefflera plant named Coveen. This new variety is a sport of the schefflera variety named Covette, itself a sport of an unnamed, commercially-available cultivar of *Schefflera arboricola.* The parent cultivar Covette is claimed in U.S. Plant Pat. No. 6,134, the contents of which are incorporated herein by reference.

The genus Schefflera includes over 150 widely-distributed species of shrubs and trees of the family Araliaceae. These species typically have compound leaves (racks), the leaflets of which are arranged finger-fashion, and are generally long-stalked. One species from Australia, *S. actinophylla,* is thought by some to comprise a separate genus (Brassaia). In any event, *S. actinophylla* is popular as a house plant, having glossy-green, lanceolate leaflets, usually 5 to 7 per cluster, that have some serration.

Another Schefflera species of Taiwanese origin, *S. arboricola* (also known as "Hawaiian Elf"), is a freely branching plant of dwarf habit, resembling when young a miniature Brassaia (*S. actinophylla*). The obovate-shaped leaflets of *S. arboricola* are arranged in racks of up to 15 cm across, comprising 7 to 8 leaflets. While the combination in *S. arboricola* of hardy dwarf habit and tree-like appearance is desirable, a dull (non-glossy) leaf has contributed to making *S. arboricola* less popular as a decorative plant than *S. actinophylla.*

The new cultivar of the present invention was discovered by me in Stuart, Fla., as a mutation of Covette. More specifically, the mutation was observed initially as a single branch growing in a cultivated area from one plant of the parent cultivar. By asexual reproduction, via soil-rooted stem cuttings, of the new cultivar in Stuart, Fla., I have reproduced the unique features of the new cultivar through successive propagations.

As asexually reproduced, the cultivar is characterized by a compact form (approximately 30 inches wide and 32 inches high) and, like the parent cultivar, further characterized by vigorous growth. The new cultivar also resembles the parent Covette in terms of foliage characteristics of leaf size, shape and texture, but differs dramatically in leaf coloration, as described in greater detail below.

DESCRIPTION OF THE DRAWINGS

The first sheet depicts a typical specimen of Coveen contained in a 10" pot;

the second sheet depicts a typical specimen of the non-variegated parent cultivar, Covette;

the third and fourth sheets depicts typical leaved branches of both Covette (on the left) and Coveen (on the right); and the fifth sheet depicts two leaved branches of Coveen and a leaved branch of Covette therebetween.

DETAILED BOTANICAL DESCRIPTION

The accompanying colored photographs illustrate the new cultivar and clearly show, the differences in plant form and foliage that distinguish the new cultivar from its parent.

The photograph comprising sheet 1 is a perspective view of a schefflera plant, approximately six months in age, of my new cultivar Coveen. The photograph comprising sheet 2 is a close-up, comparative view of foliage racks of the parent cultivar, Covette. The photograph was taken in direct sunlight.

The photographs comprising sheets three and four show the range of leaf varigation of Coveen, the new variety always being distinguishable, however, from its parent, Covette.

The present detailed description of my new Schefflera cultivar is based on plants produced according to commercial practices in the test fields of Florida Cuttings, Inc. (Stuart, Fla.). Color references are made to The Royal Horticultural Society Colour Chart (R.H.S.) except where general color terms of ordinary dictionary significance have been used. Coveen may be distinguished from other varieties by plant size, color, disease resistance and general plant characteristics.

The new cultivar Coveen has certain characteristics of Covette, but is clearly distinguishable from Covette by its distinct two-color leafs.

The leaves of the new cultivar are generally smooth-edges and lacking in serrations, as are the leaves of the parent Covette. But unlike the parent cultivar, the nature leaves of which all are a uniform dark green (approximately RHS 147A), the new cultivar Coveen is characterized by a mixed foliage of dark green leaves, leaves that are bright yellow (approximately RHS 11A in color), and leaves that present an irregular, variegated coloration combining the dark green of the parent foliage with the aforementioned bright yellow.

In a mature Coveen plant, variegated and solid yellow leaves are prominent. About ¼ to ⅓ of the leaves are yellow or yellow-green. About ⅔ to 182 are green. Referring to the Royal Horticultural Society Colour Chart, Coveen's leaf coloration is approximately 503/2 (creamy yellow) and 000 1060/1 (dark green). The stem is green to yellow green, with purplish discontinuities.

As can be seen from the drawing, the foliage of Coveen is characteristically expressed in a range of patterns with some leaves on racks being all green and others all yellow; while variegated leaves on the same racks are colored so as to present a laminated appearance. While the exact source of this effect has not been determined, it may be due to differences in chlorophyll content from one mesophyll cell layer to the next. White or light yellow leaf portions are believed to have little or no chlorophyll in each cell layer making up the leaf. Dark green leaves or portions of leaves which normally occur centrally within or from the midrib of leaves, are believed to be of normal chlorophyll content in mesophyll layers closest to the surface, and probably in each layer. Layers of intermediate color shades, are believed to be caused by at least one cell layer having little or no chlorophyll which overlies at least one layer which contains normal chlorophyll content. As many as four distinct colors may occur in characteristically unpredictable patterns which occur in distinct shades from yellow to deep green, with possibly two intermediate green shades. Similar patterns are apparent on both top and bottom surfaces, but appear to be confined to leaves.

This chimera appears to be of the replacement or vegetative (somatic) type. The source of color differences in leaf tissue may and appears to be due to differences in a genetic capacity for growth rate and chlorophyll production in adjacent layers of histogenic tissue in the meristematic dome, from which bract leaves are formed. The ultimate coloration of the individual leaves is believed to be developed based on the genotype of the layer of the tissue from which leaf primordia is developed, resulting in developed leaves of solid light yellow, solid green, or leaves having variegations with light yellow, solid green and at least one intermediate green color.

In other aspects, such as leaf length, leaf shape and internodal distance, the new cultivar is like Covette in being situated in appearance somewhere between *S. antinophylla* and *S. arboricola.* The stem color of *S. actinophlla,* for example, has a decidedly purple tinge, while the *S. arboricola* stem color is a solid, medium green. The stem color of my new cultivar, on the other hand, is dark green with purple discontinuities.

Also like Covette, the new cultivar is unusually disease- and pest-resistant. For example, the new cultivar will flourish without treatment with pesticides over an extended period, which would leave the parent, if similarly untreated, severely damaged by aphids and other insects. Unlike *S. actinophylla,* Coveen is resistant to a wide variety of diseases, including scale, and is generally resistant to infestation, e.g., by spider mites which typically infest *S. actinophylla* plants.

The characteristic distinguishing Coveen from its parent Covette is leaf coloration. The glossy-textured tri-colored leaves of Coveen differ dramatically in appearance from the uniformly green colored (RHS 147A) Covette leaves. Leaves of Coveen possess a yellow finger or fingers (RHS 11A) on ¼ to ⅓ of leaves.

Variegated varieties usually indicate a lower level of chlorophyll, which slows the growth of the plant. This is not true of Coveen, however. Coveen's growth rate is more than double that of variegated *Schefflera arboricola* and is the same as for Covette.

The most important distinguishing characteristics of Coveen are set forth in the Table, with Coveen being compared to variegated *Schefflera arboricola* and *Brassica antinophylla.*

| Foliage Description | Coveen | Varigated *Schefflerea Arboricola* | *Brassaia Antinophylla* |
|---|---|---|---|
| Leaf Shape | Oblanceolate | Obovate, with acuminate tip | Lanceolate, with acuminate tip |
| Average Leaf Length: (Approx.) | 13.3 cm | 7.4 cm | 19.3 cm |
| Leaf Texture: | Glossy | Nonglossy | Glossy |
| Leaf Thickness/ Pliability: | Medium | Hard | Soft |
| Color of Foliage (mature): | Ivy green/Barium yellow approx. 0001060/1 and 503/2 | Ivy green/Desden Yellow approx. 0001060/2 and 64 | Spinach green Approx. 0960 |
| Average Stem Length (approx): | 18.3 cm | 9.7 cm | 24.1 cm |
| Internodal Distance | 5.0–7.6 cm | 2.5–4.4 cm | 1.9–6.3 cm (significant variation) |
| Ribs & Veins | Larger and fewer than parent: about 1.9 cm apart | Many tiny veins: about 0.6 cm apart | Many small veins: about 0.6 cm apart |
| Leaflets (and coverage) per rack: | 7–8 (up to 25 cm) | 7–8 (up to 15 cm) | 5–7 (up to 30 cm) |
| Disease & Pest Resistance: | Generally resistant to disease and infestation | susceptible to aphids, disease and pests | susceptible wide variety of disease and pests |

Measurements conducted together, during daylight sun on December 10, 1991 in Stuart, Florida. Color analyzed using the Horticultural Coulour Chart, copyright 1941.

I claim:

1. A new and distinct cultivar of *Schefflera arboricola* named Coveen, as herein shown and described.

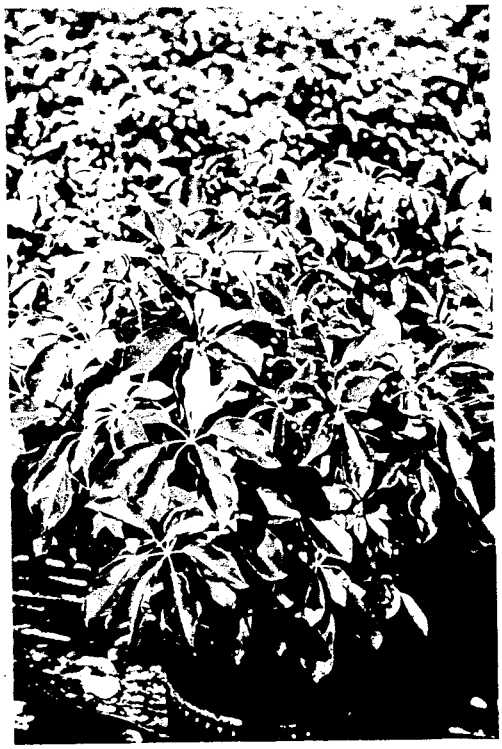

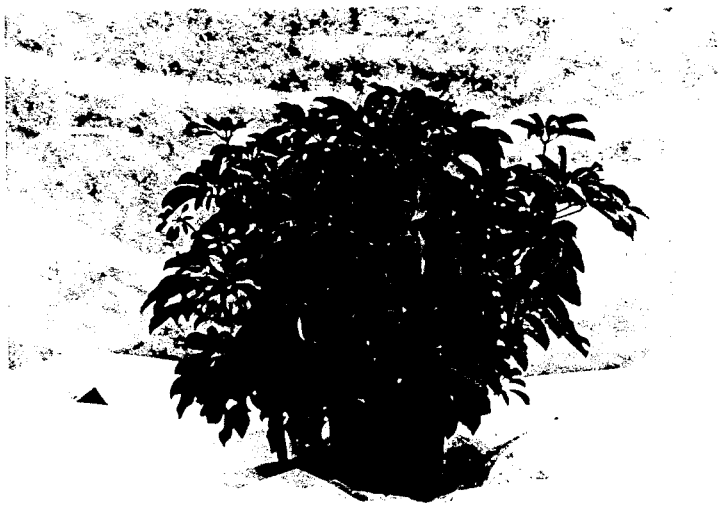

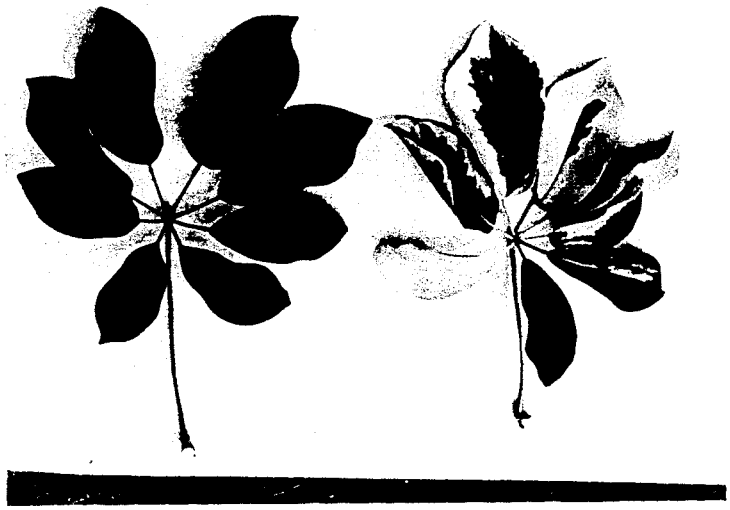

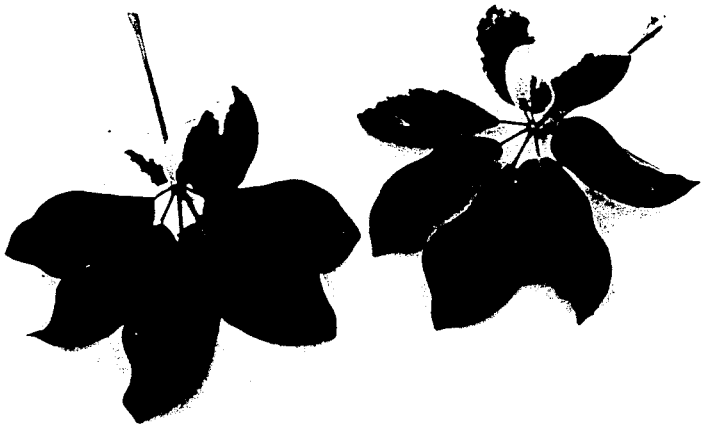

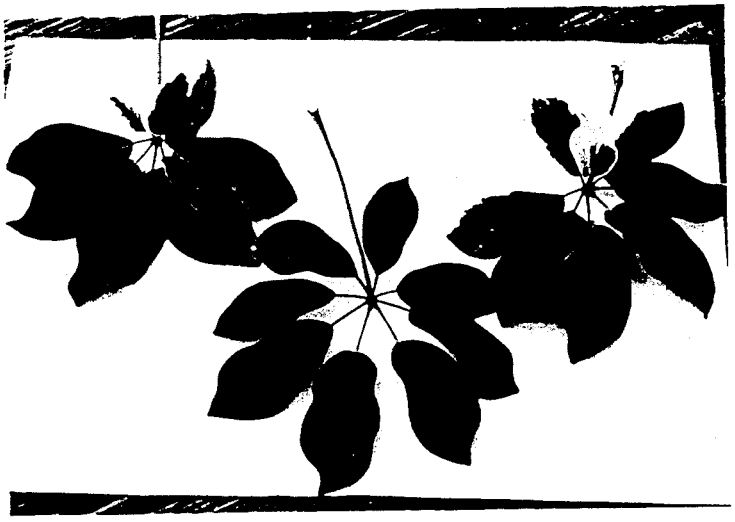

* * * * *